US006557196B2

(12) United States Patent
Falbo, Sr. et al.

(10) Patent No.: US 6,557,196 B2
(45) Date of Patent: *May 6, 2003

(54) PATIENT SUPPORT APPARATUS AND METHOD FOR PERFORMING DECUBITUS BREAST BIOPSY

(75) Inventors: Michael G. Falbo, Sr., Gladstone, MO (US); Gary H. Baker, Fortuna, CA (US)

(73) Assignee: Medical Positioning, Inc., Kansas City, MO (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/038,481

(22) Filed: Jan. 2, 2002

(65) Prior Publication Data

US 2002/0056160 A1 May 16, 2002

Related U.S. Application Data

(63) Continuation of application No. 09/712,475, filed on Nov. 14, 2000, now Pat. No. 6,367,104, which is a continuation of application No. 09/611,983, filed on Jul. 7, 2000, now Pat. No. 6,317,266.

(51) Int. Cl.[7] .................................................. A61B 6/04
(52) U.S. Cl. ............................... 5/601; 5/613; 378/209
(58) Field of Search ....................... 378/37, 209; 5/600, 5/601, 604, 612, 613, 622, 624, 185, 611

(56) References Cited

U.S. PATENT DOCUMENTS

| 4,387,888 A | 6/1983 | Marinakis |
| 5,046,708 A | 9/1991 | Schaefer |
| 5,133,338 A | 7/1992 | Wess et al. |
| 5,184,363 A | 2/1993 | Falbo, Sr. |
| 5,208,928 A | 5/1993 | Kuck et al. |
| 5,275,176 A | 1/1994 | Chandler |
| 5,461,739 A | 10/1995 | Falbo, Sr. |
| 5,609,152 A * | 3/1997 | Pellegrino et al. ............. 378/37 |
| 5,803,913 A | 9/1998 | Khalkhali et al. |
| 5,919,131 A | 7/1999 | Smoler et al. |
| 5,950,262 A | 9/1999 | Smoler et al. |
| 6,102,866 A | 8/2000 | Nields et al. |
| 6,298,506 B1 * | 10/2001 | Heinold et al. ............. 378/209 |

* cited by examiner

*Primary Examiner*—Michael F. Trettel
(74) *Attorney, Agent, or Firm*—Hovey Williams LLP

(57) ABSTRACT

A method and apparatus for obtaining mammographic images of a human patient's breast and subsequently obtaining tissue samples for biopsy includes a deck having one or more access sites, with the deck elevated above a floor or other supporting surface and capable of supporting the patient thereon. The deck includes a frame and may include one or more filler sections occupying respective access sites when closed. The filler sections are preferably positioned to provide one or more access sites on each side of the deck when opened, the access sites being sized to accommodate a technician or mammography device therein. The deck may include a central, longitudinally extending spine with crossmembers extending perpendicular thereto. The filler sections can be removably or pivotally mounted on hinges or pivot pins to selectively shift out of the openings, such as by dropping or raising to a vertical orientation, to accommodate a mammography device or examiner. Removable head and foot supports may be interchangably mounted at either end of the deck, allowing either end to receive the patient's head. The head support is specially shaped to allow oblique and cranial-caudal imaging with the patient in the decubitus position. The method includes placing the patient in a left or right lateral decubitus position to present her breast in facing relationship to a mammography device positioned in one of the access sites for obtaining a mammographic image, and if necessary, inserting a probe such as a needle or wire for needle localization or a core-cutting rotatable blade to obtain a tissue sample for biopsy.

26 Claims, 11 Drawing Sheets

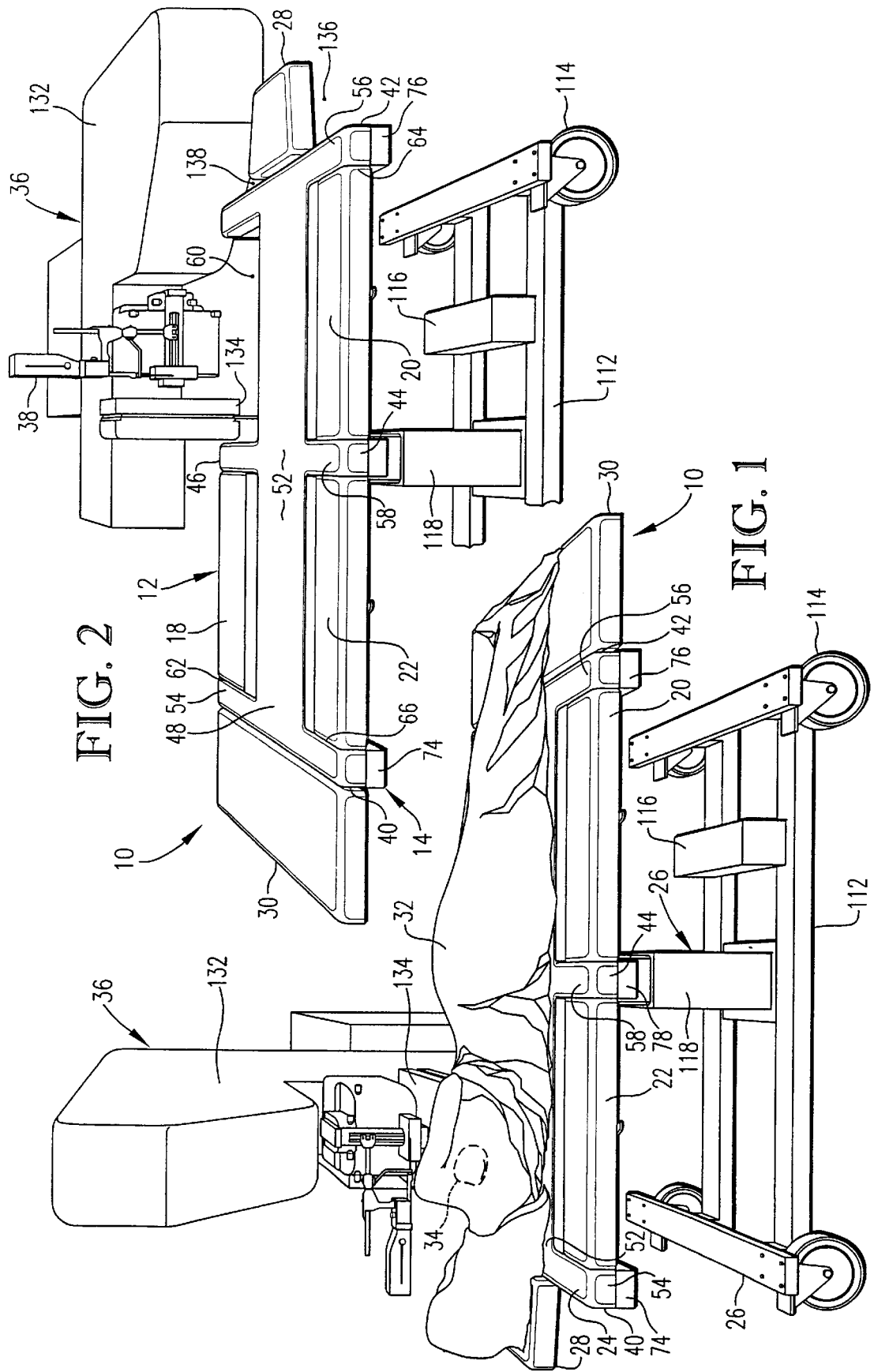

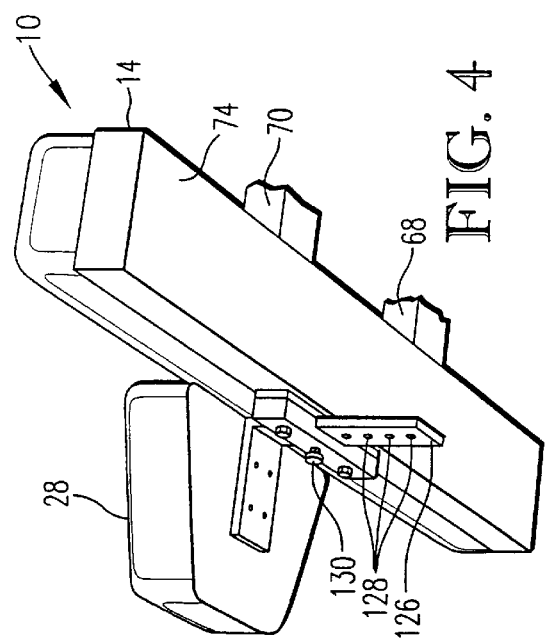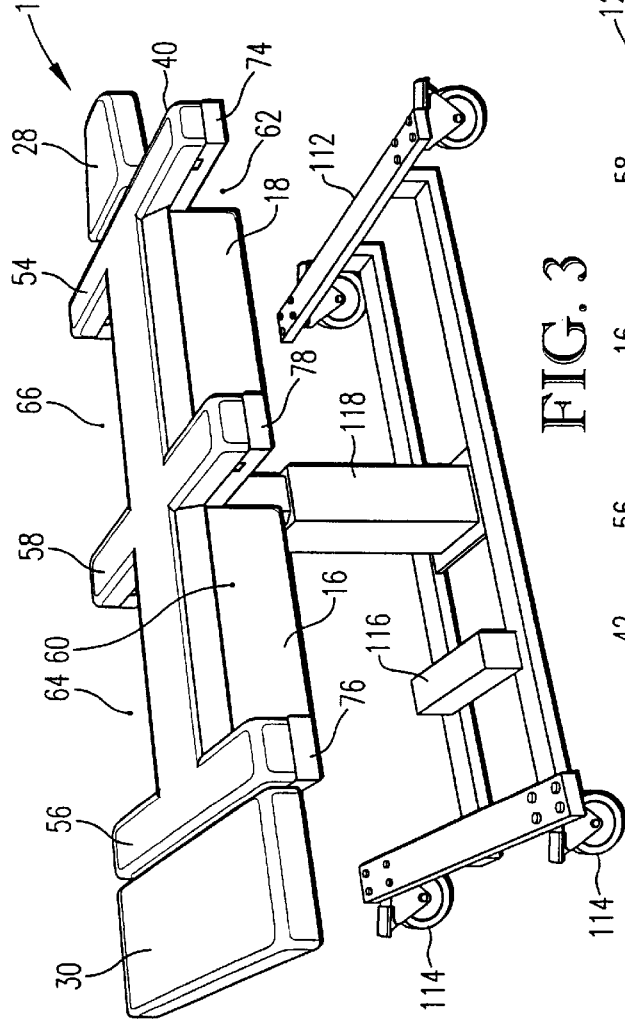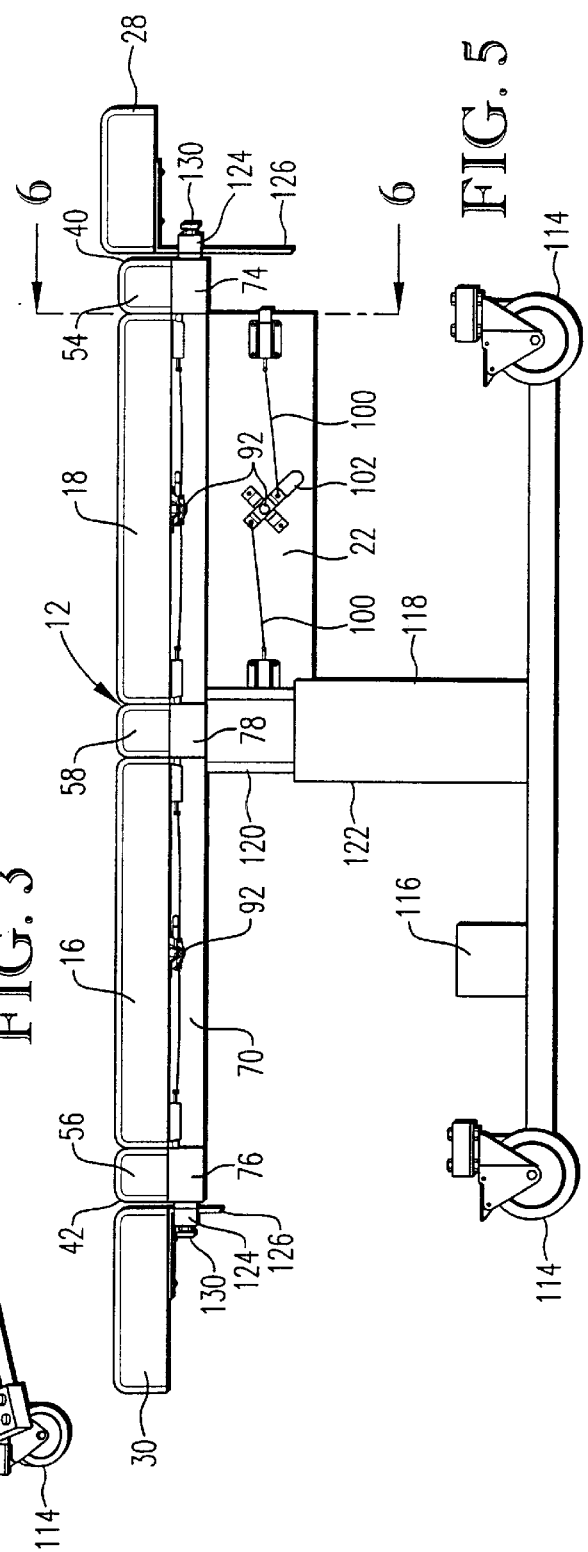

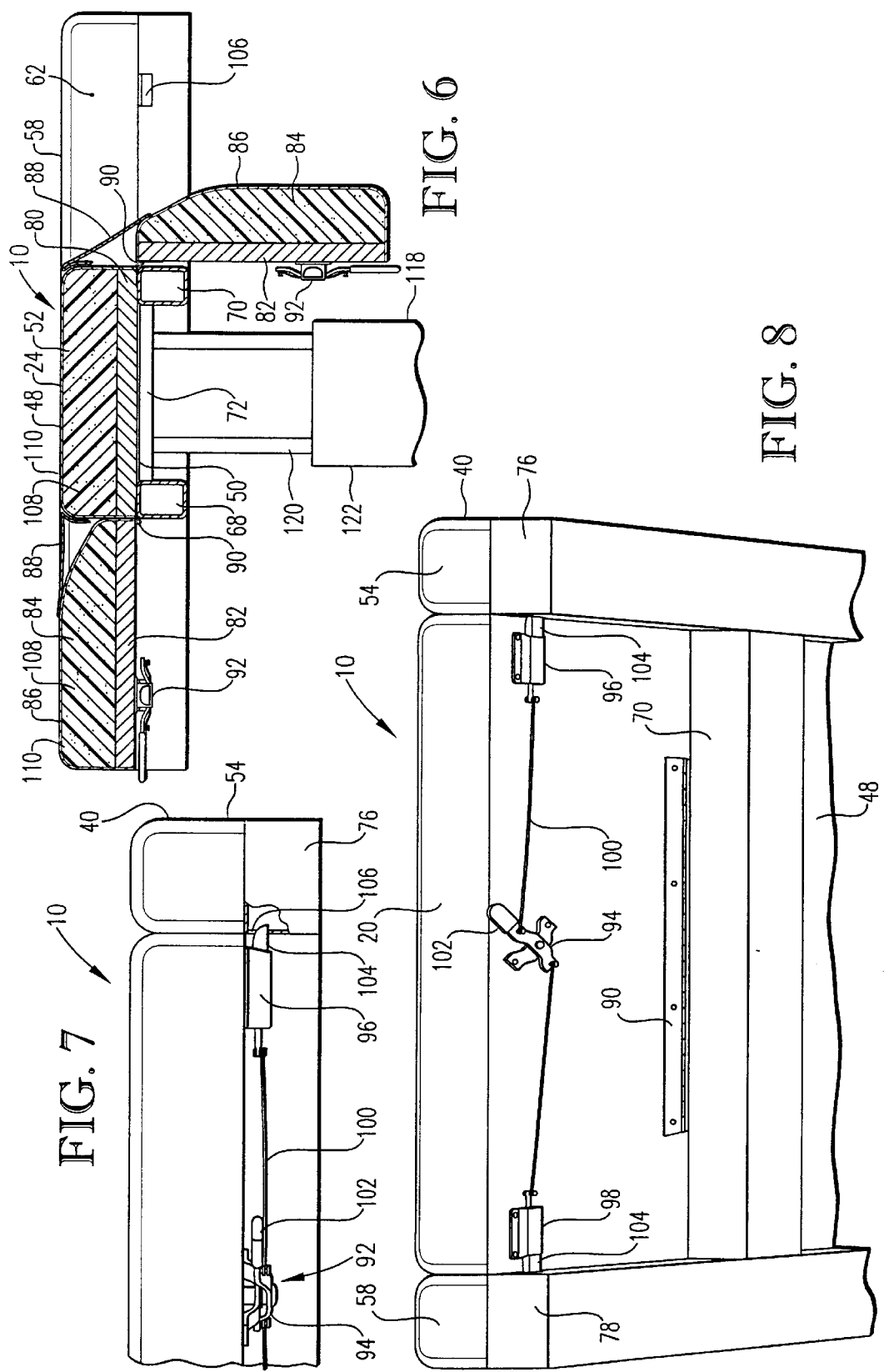

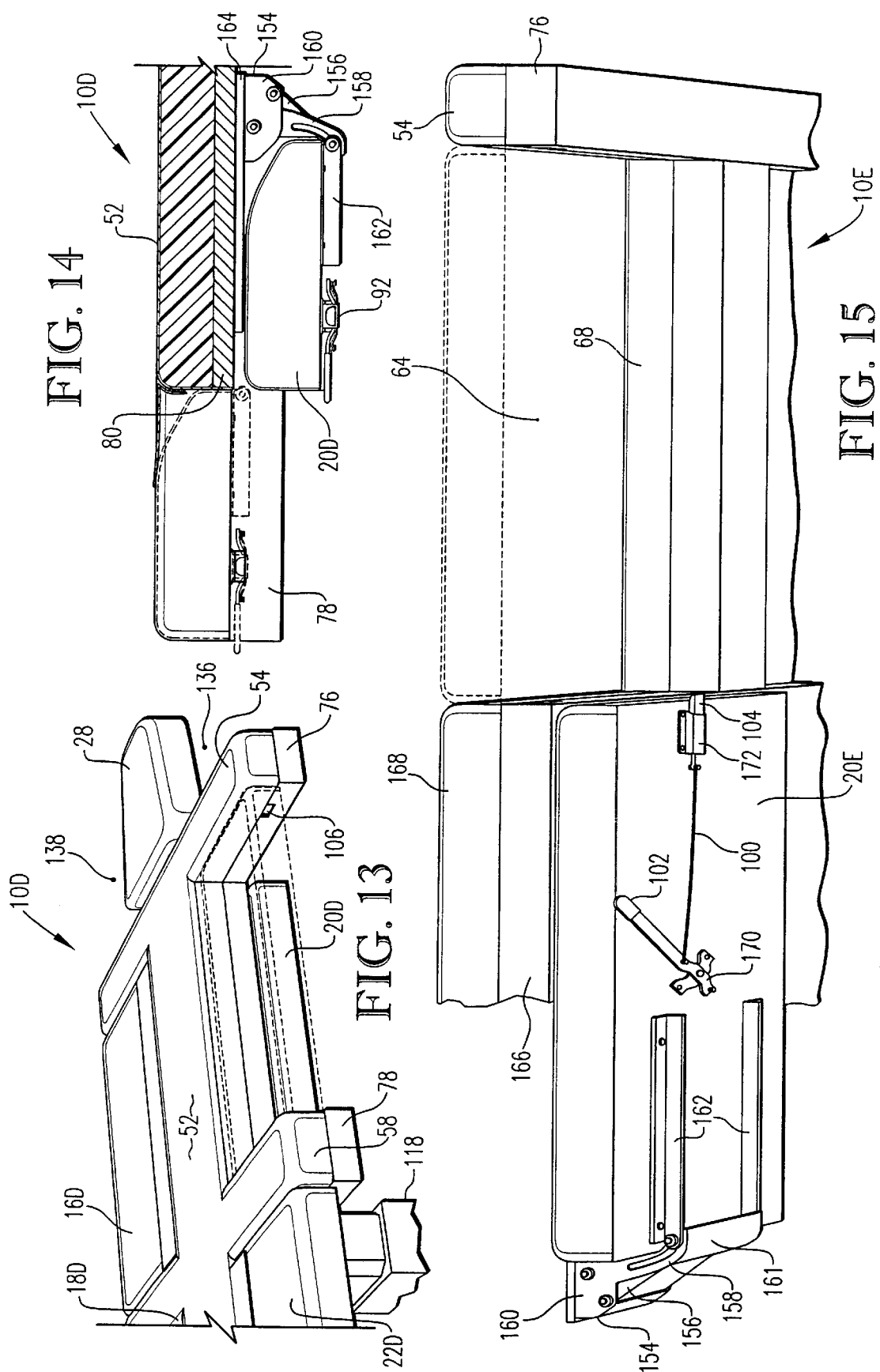

PATIENT SUPPORT APPARATUS AND METHOD FOR PERFORMING DECUBITUS BREAST BIOPSY

This is a continuation of application Ser. No. 09/712,475, filed Nov. 14, 2000, now U.S. Pat. No. 6,367,104, issued on Apr. 9, 2002, which is a continuation of application Ser. No. 09/611,983 filed Jul. 7, 2000, now U.S. Pat. No. 6,317,266.

BACKGROUND OF THE INVENTION

1. Field of the Invention

The present invention concerns a support apparatus and method for performing mammograms and breast biopsies with the patient positioned in the decubitus position. More particularly, it is concerned with a support apparatus which provides excellent patient support and access by both a technician and a mammography machine during the performance of decubitus breast mammography and biopsy procedures.

2. Description of the Prior Art

The women's health field has increasingly benefitted from advances in the field of mammography which enables early detection and treatment of cancerous and precancerous tissues. When a mammogram is taken, it is analyzed by a radiologist and if suspicious images are found, a biopsy of the tissue is taken. Mammography has been typically performed with the patient in the standing position, and the breast positioned between two opposed plates which flatten the tissue and hold it in place. Detection of suspicious tissue has then required that the physician mark the precise area to be biopsied and send the patient to the operating room. This procedure necessitated inserting a needle into the breast, and feeding of a wire through the needle which remains in place until the biopsy is performed, typically at a remote location.

An improved method for performing breast biopsies is the core biopsy technique. Again, the patient is standing or sitting in an upright position, wherein the biopsy is taken by positioning the patient with her breast between the opposed plates of a mammography device, and then, using a medical instrument (hereinafter referred to as a "breast tissue sampler"), a core of tissue is cut at the position indicated by the mammogram. This procedure represents a significant advance, in that the patient is not required to remain with a wire projecting from her breast or move to a remote location for the surgical biopsy, but rather can have it performed in the same physical area as the initial mammogram.

One problem with such procedures is that during the performance of the core biopsy, the patient can move slightly, or worse to faint. Such vasovagal reactions present significant problems both for the patient and the technician or radiologist.

One alternative support table for supporting a patient during core breast tissue sampling is a table with a central, surrounded and not laterally accessible opening therein, wherein the patient lies in a prone position with her breasts hanging through the opening. This support table, known as a "prone table" or "Parker table", is large and not readily repositionable, making access to the breast region difficult, and presents a problem in attempting to locate tumors where the patient is small breasted or the suspected tumor is adjacent the chest wall, i.e., the ribcage area.

Thus it would be beneficial if the patient could have mammograms, needle localizations and core biopsies performed when laying on her side. This is known as the decubitus position, wherein the patient's breast is oriented toward the mammogram—preferably with the upper breast positioned for mammography or biopsy, but sometimes with the lower breast examined. The patient may thus be positioned in a left lateral decubitus (left side of patient down) or right lateral decubitus (right side of patient down) to present her breast to for examination. This may require the patient to position her head at either end of the support, or to rotate longitudinally (with feet and head remaining at the same relative ends of the bed) to present the breast in the proper position. The patient must be adequately supported and this support must be provided without giving the patient a sense of anxiety about falling off the support. Additionally, the support must permit access by the technician and access to the mammography and core biopsy machine to enable performance of the mammogram and/or biopsy procedure.

Prior art patient supports are perhaps best shown in U.S. Pat. Nos. 5,184,363 and 5,461,739 to Falbo, Sr., and 5,950,262 to Smoler et al., the disclosures of which are incorporated herein by reference. Such supports are beneficially configured with drop-out sections to permit access by the technician to the patient. However, these patient supports are not configured to meet the peculiar demands of decubitus breast mammography and biopsy. For example the U.S. Pat. No. 5,184,363 discloses a support bed useful for cardiac sonography having two drop-out sections, the first to permit sonographic diagnosis of a patient lying on the bed, the second to accommodate the legs or other aspect of a person performing the diagnosis. However, the openings do not admit access by a mammography and core biopsy device, nor is the table particularly configured to permit alternate positioning of the patient on either the left or right side. Moreover, a mammography device often must be tilted wherein a bulky portion must lie adjacent the patient's head and below the top surface of the table, which is not possible with the aforementioned support bed. The U.S. Pat. No. 5,461,739 support apparatus is also designed for performing cardiac sonography, but with the patient in a supine position (resting on the back) and accommodating a pedaling device. It also teaches the use of one, or alternatively two, patient drop-out sections, but is not configured to admit into the openings a mammography and core biopsy device, nor to allow the patient to rest in a variety of different positions to present the breast for examination.

There has thus developed a need for an improved patient support apparatus which is designed for the performance of mammography, needle localizations and breast biopsies with the patient in a decubitus position. There has also developed a need for an improved method of performing mammography and breast biopsy which allows the patient to have the mammography and/or breast biopsy performed with the patient in a decubitus position.

SUMMARY OF THE INVENTION

These needs have largely been met by the method and apparatus of the present invention. That is to say, the method and apparatus of the present invention permit the performance of mammography, needle localization and breast biopsy whereby the patient may be positioned for optimum imaging, provide great flexibility in space utilization, give the patient excellent support while in a decubitus position, and provide economies by permitting a single examination room to serve for mammography, needle localization and core biopsy.

The patient support apparatus of the present invention broadly includes a patient support deck including a frame and pad defining a multiplicity of openings. To provide the most flexibility and safety, the openings are preferably occupied by filler sections which are most preferably shiftably mounted to the frame to permit access by examiners and a mammography device into the openings. The filler sections may be shifted by either pivoting or translational movement, or altogether removed from the frame when an opening is desired. The deck is supported by a deck support, and head and foot supports may be mounted at opposed ends of the deck. The head support preferably has a smaller transverse dimension than the width of the bed to provide an open area adjacent the head support, thereby permitting a mammography device to be tilted into and occupy the open area during examination.

The frame and openings are arranged to provide opposite openings (and preferably corresponding filler sections) which permit ingress from the sides of the deck by examiners such as technicians, nurses and physicians, and positioning of the mammography device therein. The openings are sized and positioned to receive mammography devices therein, with the openings preferably separated by a frame member of sufficient strength to bear the weight of the patient thereon. The frame preferably includes a laterally centered, longitudinally extending spine with center and end cross-channels extending perpendicular thereto in a common horizontal plane, thereby defining at least two openings. The two openings could be located on the same side of the apparatus and thereby enable positioning of the patient to ensure that the "up" breast may be presented for imaging. The two openings could also be located on opposite sides of the apparatus, again allowing the patient to be positioned so that either breast is presented in the "up" breast position, but also allowing the examiner or other members of the technical staff to be closer to the patient when they are positioned (e.g., standing or sitting) in the opposite opening. In the preferred embodiment, four openings are provided to provide maximum utilization and flexibility, so that in even confined room configurations, the "up" breast may always be imaged and the examiner or other member of the technical staff can position themselves close to the patient through the utilization of additional openings. Filler sections include release mechanisms which permit them to be locked in a closed position to fill the opening or released whereby the opening is accessible from the side of the deck.

The method of the present invention includes positioning the patient in a decubitus position on the support apparatus, releasing as necessary one or more of the filler sections to provide access to the patient's breast by a mammography device or instrument including probes such as needles and wires for performing needle localizations or circular blades for obtaining core biopsies of breast tissue, and supporting the patient on the apparatus while a portion of the mammography device and/or breast tissue sampler is located in the opening. Advantageously, the method also includes the patient mounting the support apparatus with the filler sections within the openings to provide support, and after the patient is properly positioned thereon, clearing the opening by removing or shifting one or more of the filler sections to clear the corresponding openings. The method further includes repositioning the patient, either by rotating the patient about the longitudinal axis so that she switches the side of the apparatus she is facing, or remaining facing the same side while moving her head to the end of the apparatus where her foot was previously located. This permits examination of the other of the patient's breasts with each breast presented in an up breast position.

As a result, the support apparatus and method allow the patient to be positioned in a position most advantageous for examination of any area of either breast and allows usage of relatively small examination rooms for performing mammograms, needle localizations and breast biopsies. The patient is uniquely afforded support in her critical areas while at the same time permitting access by the examiner and mammography device to optimize the imaging and retain the feeling of patient security. These and other objects will be readily appreciated by those skilled in the art with reference to the drawings and description which follow.

BRIEF DESCRIPTION OF THE DRAWINGS

FIG. 1 is a front perspective view of a first embodiment of the patient support apparatus of the present apparatus, showing a patient presenting for mammography in a left lateral decubitus position;

FIG. 2 is a fragmentary front perspective view similar to FIG. 1 with the patient removed to show the positioning of the support apparatus and mammography/breast biopsy device for a patient in a right decubitus position;

FIG. 3 is a perspective view of the patient support apparatus taken proximate the foot support end and showing the four access openings available for ingress of equipment or personnel;

FIG. 4 is an enlarged, fragmentary bottom perspective view showing the head support mount of the apparatus hereof;

FIG. 5 is a side elevational view of the patient support apparatus with filler sections oriented in a closed and supporting position;

FIG. 6 is an enlarged vertical sectional view taken along line 6—6 of FIG. 5 showing the support pillar, spine, and two opposed pivotally mounted filler sections, one in a closed and supporting position and one in an open access position, of the patient apparatus hereof;

FIG. 7 is an enlarged fragmentary elevational view in partial section showing the release mechanism for pivotal movement of the filler sections of the patient support apparatus hereof;

FIG. 8 is an enlarged, fragmentary bottom side perspective view showing the mechanism for enabling release and pivoting of the filler sections from a substantially horizontal closed position to a substantially vertical open position;

FIG. 13 is a fragmentary top side perspective view of the embodiment of FIG. 12, showing the position of the filler section when stowed in solid lines and showing the position of the filler section occupying the opening in phantom lines;

FIG. 14 is a fragmentary side elevational view of the embodiment of FIG. 12 similar to that shown in FIG. 6, but showing the coupler permitting the filler section to translate outwardly and rise upwardly to occupy its corresponding opening;

FIG. 15 is a fragmentary bottom side perspective view of a sixth embodiment of the apparatus hereof, showing the coupler of FIGS. 12–14 oriented for translation of a filler section in a longitudinal direction;

DESCRIPTION OF THE PREFERRED EMBODIMENT

Figure 9:
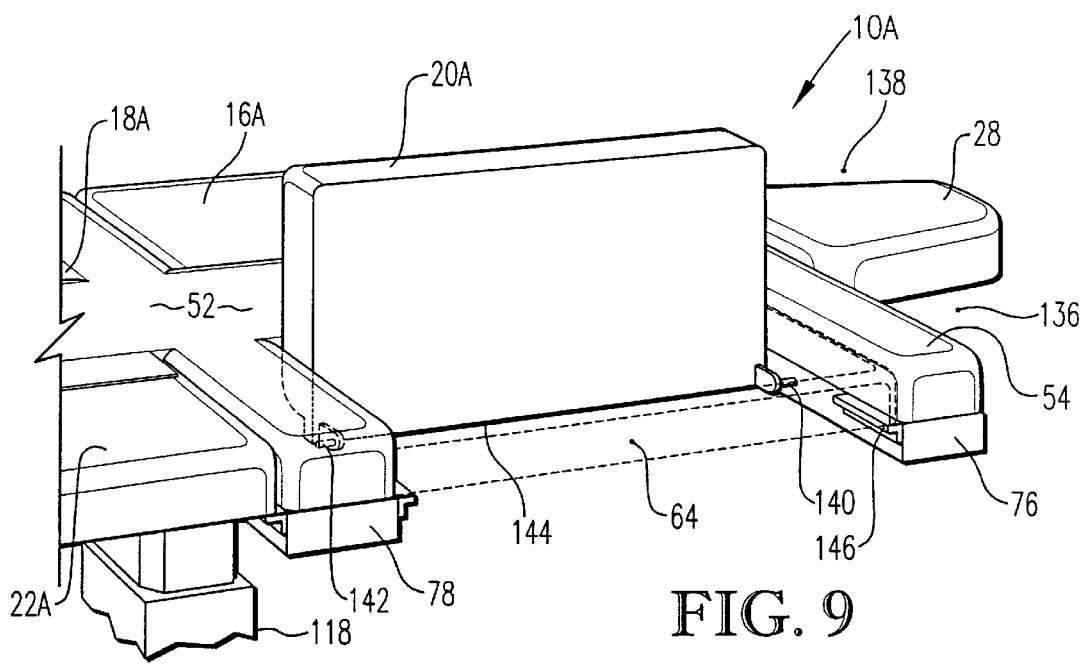
FIG. 9 is an enlarged, fragmentary top side perspective view of a second embodiment of the apparatus hereof, wherein one or more of the filler sections are pivotally mounted to swing upwardly to provide a support for a patient positioned in a decubitus position and to permit access by an examiner therein.

Referring now to the drawings, a patient support apparatus 10 for use in the performance of mammography and breast biopsy broadly includes a deck 12, the deck 12 including a frame 14, a multiplicity of filler sections 16, 18, 20 and 22, and a pad 24 overlying the frame 14 for cushioning the patient thereon. The deck 12 is elevated above the floor or other supporting surface by a deck support 26. Advantageously, a head support 28 and a foot support 30 may be coupled to respective ends of the deck 12. The patient support apparatus 10 is sized to support an adult human patient 32 thereon, and is especially configured for supporting the patient to permit her to present her breast 34 to a mammography device 36 to which a breast tissue sampler 38 may be attached. The device 36 is positioned in an access site within the deck 12 when one or more of the filler sections is shifted or removed, thereby enabling the patient 32 to be supported by the apparatus 10 with the breast in an optimum position for imaging by the device, as shown in FIG. 1.

While multiple embodiments are shown of the present invention, with like numbers used to refer to the same components, it is to be understood that all are sized and configured to support a human patient thereon, and to accommodate a mammography device and mammotome or an examiner or other member of the technical staff during mammography, needle localization or obtaining a tissue sample. Thus, while the patient 32 is shown only in FIG. 1 and the device 36 shown in FIGS. 1 and 2, each embodiment of the apparatus 10 is adapted for supporting the patient and use with the device.

In greater detail, the deck 12 is configured with a first end 40 and an opposite second end 42, a first preferably linear side 44, an opposing second preferably linear side 46, a top surface 48 and a bottom surface 50. A longitudinal spine 52 extends between the first and second ends and is preferably centered between the first and second sides. The deck 12 further includes a first outer support arm 54 adjacent the first end 40, a second outer support arm 56 adjacent the second end 42, and a central support arm 58 positioned intermediate the arms 54 and 56. The support arms 54, 56 and 58 are preferably oriented perpendicular to the spine 52, and together define four recesses extending inwardly from the sides 44 and 46 to provide openings 60, 62, 64 and 66 which may receive therein respective filler sections 16, 18, 20 and 22.

The frame 14 includes a framework of preferably metal, tubular channels including longitudinally extending substantially parallel rails 68 and 70 interconnected by plate 72, first and second end cross-channels 74 and 76, and center cross-channel 78. The rails and cross-channels thus provide stiffness and support for the spine and arms as a part of the deck 12. The tubular channels are interconnected by welding or mechanical fasteners whereby the channels 74, 76 and 78 are oriented perpendicular to the rails 68 and 70 as shown in FIG. 6. In addition, FIG. 6 shows a rigid panel 80 of wood, plastic, metal or other substantially rigid material is attached to and overlies the rails 68 and 70 and cross-channels 74, 76 and 78. As shown in FIG. 6, the panel 80 serves both to support the pad 24 and rigidify the deck 12. The panel 80 is shaped and sized to provide the four openings 60, 62, 64 and 66 and to receive the filler sections 16, 18, 20 and 22 therein, each opening most preferably being at least about 18 inches and more preferably about 22 inches or greater longitudinally and preferably about 10 inches across in order to accommodate a currently available mammography device or an examiner therein. Each opening 60, 62, 64 and 66 thus defines an access site for the mammography device 36, examiner or patient. Although only one, two or three openings may be provided in the apparatus 10, the openings 60, 62, 64 and 66 are preferably located so that two openings are located along each side to permit access, and in substantially opposed pairs so that opening 60 is opposite opening 64 and opening 62 is across from opening 66. Each pair of openings is thus preferably separated by spine 52 and the openings along each side are preferably separated by central support arm 58.

The filler sections 16, 18, 20 and 22 are sized to be complementarily received in the respective openings 60, 62, 64 and 66. While the filler sections may be configured to be removably coupled to the frame 14, in the embodiment of FIGS. 1–8 and as shown in FIGS. 2, 6 and 8, the filler sections are pivotally mounted to the frame and provide access from the sides 44 and 46. To that end, each filler section 16, 18, 20 and 22 includes a sheet 82 of the rigid material such as described for panel 80, and an overlying cushion 84 of foam cushioning or the like, covered with fabric, leather, or vinyl cloth 86. The cloth 86 is slightly overlapped by a panel or web 88 of similar material, as shown in FIG. 6. Such a panel or web is shown as reference character 82a in U.S. Pat. No. 5,184,363, the disclosure of which is incorporated herein by reference. Each filler section 16, 18, 20 and 22 is pivotally connected to the frame 14 by a hinge 90, preferably but not necessarily oriented for pivoting on a longitudinally extending axis. Each filler 16, 18, 20 and 22 section further includes a release mechanism 92.

A typical, and in this case preferred, release mechanism 92 both holds the corresponding filler section in position when engaged with the frame 14 and enables the filler sections to drop and clear the respective openings from obstruction. As shown in FIGS. 5, 6, 7 and 8, the release mechanism 92 includes a release lever 94 and a pair of latches 96 and 98 connected to the release lever 94 by a connector 100 such as cables, mechanical linkages or bead chains. Upon shifting of the handle 102 of release lever 94 to the left as shown in FIG. 8, the connectors 100 actuate the latches 96 and 98 to shift their dogs 104 extending through slots 106 of the cross-channels 74, 76 and 78 as shown by FIG. 7. When the latches 96 and 98 are released and their dogs 104 are out of engagement with the channels, the filler sections may be pivoted and lowered until stopped by gravity as shown by FIG. 6.

The deck 12 includes pad 24 is shaped and configured to overlie the frame 14 for supporting the patient 32 on the spine 52 and supporting arms 54, 56 and 58 of the deck 12. The pad includes a foam cushion 108 and a cover 110 of the same material as cloth 86. By being superposed relative to the frame 14, the pad 24 provides both cushioning and support for the human patient 32 resting thereon, and positions the patient 32 on a relatively flat, cushioned, horizontal surface across the deck 12 including those areas over the filler sections as wells as the areas above the frame 14.

The deck support 26 elevates the deck 12 above a floor or other supporting surface and preferably includes a base 112 provided with lockable wheels 114 for permitting the entire patient support apparatus 10 to be easily moved or maintained in place as shown and described in U.S. Pat. No. 5,950,262, the disclosure of which is incorporated herein by reference. Thus, the apparatus may rotate about a central, upright axis, translate to carry the patient therewith, and be locked in position against movement by engaging the locking arms of the wheels 114. The base 112 carries a motor drive control 116 and a pedestal 118 connected to the frame 14 at plate 72 as shown in FIG. 6. In the preferred configuration as illustrated herein, the pedestal 118 includes telescoping sections 120 and 122 and a motorized extensible drive (not shown) which permits the deck 12 to be raised and lowered relative to the supporting surface.

Advantageously, the cross-channels 74 and 76 each include a laterally centered bracket 124 of stainless steel or the like which removably mounts either the head support 28 or the foot support 30 as shown in FIG. 4. That is, because both the head support 28 and foot support 30 include a commonly configured mounting bar 126, the head support 28 may be exchanged in position with the foot support 30, and coupled to either bracket 124. In addition, the elevation of the head support may be varied by the insertion of a locking screw 130 through one of the apertures in its mounting bar 126. It is desirable that the head support 28, shown trapezoidally shaped, be considerably narrower in width than the width of the deck 12 or pad 24 so that the mammography device 36 shown in FIGS. 1 and 2 may be tilted and the upper camera part 132 thereof may be positioned in clearings 136 or 138 proximate the head support 28 and the respective end cross-channel 74 or 76 to which the head support 28 is mounted. On the other hand, the foot support 30 may be relatively narrow and have only the width of the head support, or extend the width of the apparatus 10, as shown, as the mammography device 36 is positioned more proximate the patient's head. By providing a plurality of apertures, the head support 28 may be vertically adjusted to provide comfortable support corresponding to the patient's physique.

The apparatus 10 is configured to accommodate use with a wide variety of mammography devices which comprise one preferred environment of use. The mammography device 36 as illustrated in FIGS. 1 and 2 is a Model Senovision by General Electric Medical Division of Milwaukee, Wis. It is one example of a device 36 useful herewith and may include an integrated breast tissue sampler 38 positioned adjacent the breast compressing plates of the mammography device 36 for performing core biopsies or needle localizations while the breast 34 of the patient 32 is imaged. One breast tissue sampler 38 which may be mounted on a mammography device 36 for performing core biopsies in accordance with the present invention is a Biopsys device manufactured by Ethicon Endo-Surgery, Inc. of Cincinnati, Ohio and sold under the trademark Mammotome.

In the method of the present invention, the patient 32 is positioned on the patient support apparatus 10 so that her torso and legs are supported on the portion of the spine 52 with her head resting on the head support 28 and her feet supported either by the foot support 30 or, in shorter patients, by the spine 52 or the filler sections 18 and 20 as the apparatus is arranged in FIG. 2. Any of the filler sections 16, 18, 20 and 22 may be initially raised and locked in position to fill the corresponding openings 60, 62, 64 and 66 as illustrated in FIG. 2, so that when the patient moves onto the support apparatus 10 she has good support and a feeling of security during positioning thereon. The apparatus 10 also permits the patient to be supported by the cross-channels and one or more of the filler sections 16, 18, 20 and 22 when that filler section is in a closed position. FIG. 1 illustrates the apparatus 10 and device 36 arranged to receive a patient 32 in a left lateral decubitus position, whereby the image of the patient's upper (right) breast 34 would be achieved from the camera 132 above the right shoulder to the film cassette 134 at the patient's midline, a lateral-medial view. Once the patient 32 is in the decubitus position, as shown in FIG. 1 and preferably over the center or spine 52 of the support apparatus 10, one or more of the filler sections 16, 18, 20 or 22 may be dropped to the position shown on the right of FIG. 6 to provide access into that opening by the mammography device 36. For example, as shown in FIG. 1, the filler section 18 would be dropped to clear opening 62 to receive the device 36.

However, the support apparatus 10 hereof also permits the patient 32 to be positioned to the side of the spine 52, whereby her torso spans an opening in order to place her breast 34 in position for mammography, needle localization or breast biopsy. For example, in order to place the patient in sufficient proximity to the mammography device 36, it may be necessary for the patient to move laterally on the support apparatus so that her hips are over the central support arm 58 and her shoulders supported by one of the outer support arms 54 or 56 depending or her positioning on the apparatus 10, with a filler section dropped to clear the corresponding opening so that some or all of the patient's torso spans that opening. While the apparatus 10 may be used with the patient 32 in a sitting position, more preferably the patient is positioned in either a left decubitus or right decubitus position.

The patient's breast 34 is then placed between the clamping plates adjacent the film cassette 134 of the mammography device 36. A better image may often be obtained by imaging the upper breast, and so in the left decubitus position shown in FIG. 1, the head support 28 is positioned at first end 40 and foot support 30 at second end 42, with the head support 28 vertically adjusted to be slightly above the upper level of the pad 24 for comfort. Filler section 18 is pivoted downwardly to receive the mammography device 36 in the cleared opening 62. The right breast 34 of the patient 32 is then positioned between the clamping plates of the mammography device 36 for imaging with the breast compressed side to side and the image obtained lateral to medial. In the described position, following the imaging of the breast 34, it is also possible to perform a needle localization or core biopsy. As described above, obtaining the sample for the biopsy would be performed with the breast tissue sampler 38 sampling in the cranial caudal plane perpendicular to the plane of compression. The apparatus 10 hereof also receives a portion of the mammography equipment of other manufacturers than that illustrated, wherein it is also possible to perform core breast tissue sampling for a biopsy in the same direction as the direction of the movement of the plates during compression. The direction of the movement of the plates shown in FIG. 1 is lateral medial, whereas the direction of movement of the plates shown in FIG. 2 is cranial caudal.

Alternatively, the mammography device 36 can be tilted as shown in FIG. 2 if the radiologist desires to obtain a cranial-caudal compression image of the breast, whereby the breast is compressed from top to bottom, advantageously with the patient 32 remaining on the apparatus 10. FIG. 2 shows the apparatus 10 and mammography device 36 arranged for the patient 32 to assume a right lateral decubitus position, and the image would be obtained from the camera portion 132 adjacent the patient's head toward the film cassette 134 near the patient's waist, a cranial-caudal view. In this configuration, filler section 16 would be opened to allow receipt of a portion of the mammography device 36 in opening 60, and thus film cassette 134 and the clamping plates adjacent thereto are permitted to reach patient 32. Either filler section 18 or 20 may be opened to permit easy access by the examiner, such as a nurse, technician, physician or other qualified person to position the patient and the mammography device 36.

To obtain the mammogram of each breast 34 in a superior or upper position, the patient may be repositioned in one of two ways by using the apparatus 10 hereof, whichever is more comfortable for the patient and depending on the layout and configuration of the examination room. Starting from FIG. 1 showing the patient presenting her right breast in a superior position for imaging, one alternative available with the present apparatus 10 is that the patient 32 may turn over, rotating longitudinally, so that she faces generally toward opening 66, and the mammography device 36 is moved from opening 62 accessible from side 46 into the opening 66 accessible from side 44. The filler section 18 may thus be pivoted upwardly to a horizontal position to provide stability and support while the patient turns, and the head support 28 may remain in position. Alternatively, the patient 32 may turn so that her head moves from first end 40 to second end 42, and thus the positions of the head support 28 and the foot support 30 are exchanged as shown by the arrangement in FIG. 2. In this option, the mammography device 36 is merely shifted from its initial location in opening 62 into opening 60 as shown in FIG. 2. The patient is thus in a right decubitus position with her left breast uppermost, and again her breast is placed between the clamping plates of the mammography device 36 (with either lateral-medial or cranial-caudal compression as described above) so that an image is obtained. A comparison of FIG. 1 with FIG. 3 illustrates a third option, whereby the entire apparatus 10 may be moved on its wheels about a generally upright axis so that the relative positions of the first end 40 and second end 42 are exchanged without the need for repositioning the head support 28 and the foot support 30, and the patient 32 then turns about her longitudinal axis and either the device 36 or the entire apparatus 10 is shifted laterally so that a portion of the mammography device 36 is received into opening 66 illustrated in FIG. 3.

During any part of the mammography procedure, not only can the patient and mammography device be repositioned, but also the filler sections occupying openings and below the patient may be dropped to permit the examiner to work without undue bending or stretching in order to prepare the mammography device and position the patient's breast therein for mammography, needle localization or biopsy. In this regard, the legs or torso of an examiner may occupy any one of the openings not occupied by the mammography device 36 in the same manner as illustrated with regard to the examiner 96 shown in FIG. 5 of U.S. Pat. No. 5,950,262.

Further, because the deck support 26 elevates the deck 12 above the floor or other supporting surface and the openings are configured to receive the cassette portion 134 of the mammography device 36 medial to the sides 44 and 46 depending on which opening is utilized, the apparatus 10 facilitates use of the mammography device 36 for stereo imaging of the breast when the patient is in a decubitus position. Stereo imaging of the breast typically involves taking two images of the breast to obtain a three dimensional representation of the location of any questionable tissue within the breast. When the patient is in the decubitus position and stereo images in a cranial caudal direction are desired, the mammography device 36 may be oriented to take images with the camera portion 132 positioned below the deck 12 and angled upwardly toward the film cassette portion 134 at an angle of about 15° from that shown in FIG. 2. Then, to obtain the second, stereo image, the mammography device 36 may then swing so that the camera portion 132 is above the deck 12 and angled downwardly toward the film cassette portion 134 at an angle of about 15° from that shown in FIG. 2, so that about a 30° angle between the first and second images is obtained.

If the results of the mammogram reveal suspicious tissue to the radiologist and a biopsy is required, the core biopsy may be obtained with the patient 32 positioned as described above. Typically, during core biopsy, stereotactic images are obtained to provide a three-dimensional image of the tissue and localization of the lesion. Because the breast tissue sampler 38 may be mounted on the mammography device 36 and its position precisely controlled, the insertion of the probe to obtain the core biopsy may be performed with the patient positioned most favorably to obtain access to all breast tissue and conducted in the same room where the initial mammogram is performed. Depending upon the particular mammography device 36 used, the biopsy needle may be introduced in the plane parallel to the axis of compression as shown in FIG. 2, or perpendicular to the axis of compression. After obtaining the core tissue sample, a tissue analysis is performed as is known to those skilled in the art.

Figure 10:
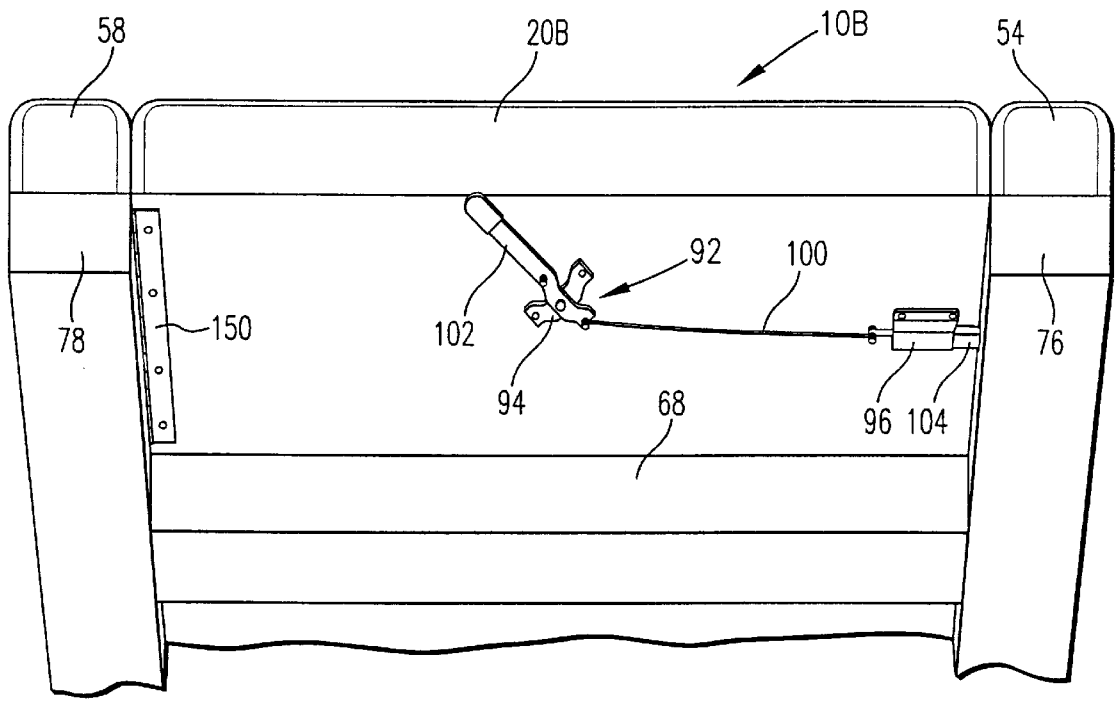
FIG. 10 is an enlarged, fragmentary bottom side perspective view showing a third embodiment of the apparatus hereof, wherein one or more of the filler sections are pivotally mounted to pivot downwardly about an axis transverse to the longitudinally extending spine and provided with a release mechanism.

A number of different options are available for shifting a filler section to clear an opening, as illustrated by the alternative embodiments shown in FIGS. 9 through 25. In the embodiment of the apparatus 10A shown in FIG. 9, one or more of the filler sections 16A, 18A, 20A and 22A may be pivotally mounted to swing upwardly rather than downwardly to clear its corresponding opening. Thus, apparatus 10A shown in FIG. 9 includes a filler section 20A having pivot pins 140 and 142 adjacent the inboard side 144 and coupled to cross channels 76 and 78, respectively. Ledges 146 and 148 are welded, screwed, or otherwise fastened to the cross channels 76 and 78 to provide support when the filler section 20A is horizontal, as shown in FIG. 10. When the filler section 20A is pivoted upwardly as shown in FIG. 9, it may provide support against which the patient may lean when in a lateral decubitus position.

FIG. 10 illustrates a third embodiment of the apparatus 10B, which is similar to apparatus 10, but wherein the filler section 20B is coupled by a hinge 150 to center cross channel 78 to pivot downwardly about an axis transverse to the longitudinal axis of the spine 52. When in the up, horizontal position occupying opening 64, the filler section 20B is supported opposite hinge 150 by the dog 104 of the latch 96 extending into a slot in one of the end cross channels, e.g. cross channel 76. As shown in FIG. 10, any of the filler sections may be provided with a release mechanism 92. To clear the opening 64, the handle 102 is shifted to the right as seen in FIG. 10, thereby releasing the dog 104 of latch mechanism 96 to permit the filler section 20B to swing downwardly.

Figure 11:
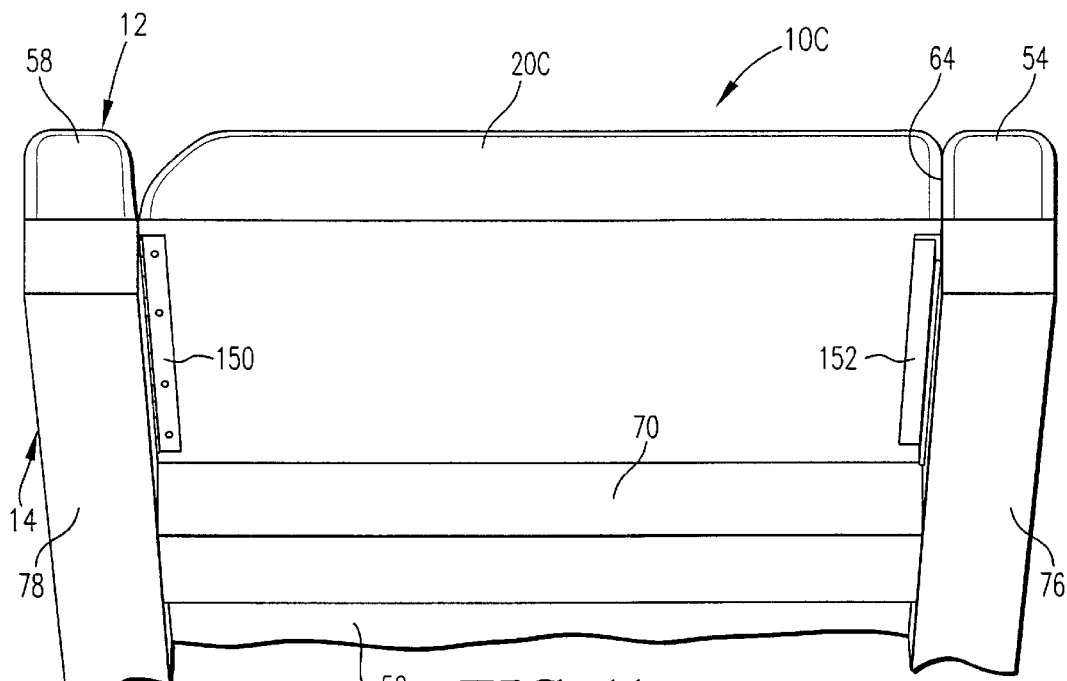
FIG. 11 is an enlarged, fragmentary bottom side perspective view showing a fourth embodiment of the apparatus hereof, wherein one or more of the filler sections are pivotally mounted to pivot upwardly about an axis transverse to the longitudinally extending spine and provided with a support ledge opposite a hinge.

FIG. 11 illustrates a fourth embodiment of the apparatus 10C similar to apparatus 10B, but wherein one or more of the filler sections, for example filler section 20C, may be pivotally coupled to the center cross channel 78 to swing upwardly out of its opening 64. A hinge 150 is attached by welding, screws or other attachments to the center cross channel 78 and a ledge 152 is welded or fastened to the opposite end cross channel 76.

Figure 12:
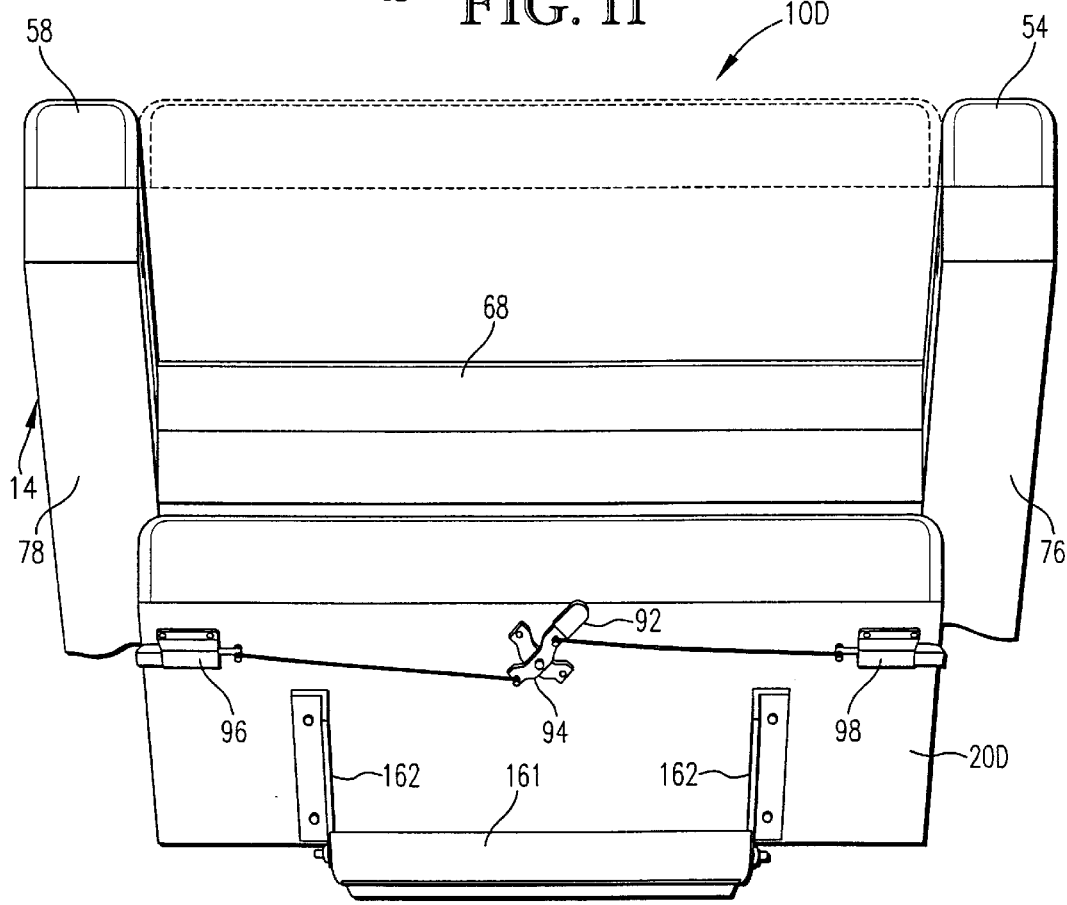
FIG. 12 is an enlarged, fragmentary bottom side perspective view showing a fifth embodiment of the apparatus hereof, wherein the width of the longitudinally extending spine is widened and one or more of the filler sections have a coupler for translating and dropping the filler section from the opening for stowage beneath the spine.

FIGS. 12, 13 and 14 show a fifth embodiment of the apparatus 10D wherein one or more of the filler sections, shown as filler section 20D, is configured to drop and slide laterally toward and beneath the spine 52 to clear the corresponding opening 60. In this embodiment, the spine 52 would be of sufficient width to permit the filler section 20D to be received therebeneath. Mount 154 includes arms 156 and 158 on each side thereof which are pivotally coupled to a bracket 160 and to bed 161 attached to a pair of supports 162 attached to the underside of filler section 20D, whereby the filler section 20D is maintained in a generally horizontal orientation if desired, or because of the arcuate slots provided in the arm 158, may be angled if desired. The brackets 160 each slide along a respective track 164 mounted to the panel 80, whereby the filler section 20D slides along the tracks 164 from the position shown in solid lines in FIG. 14 until it reaches the outboard end of the tracks, then swings on arms 156 and 158 to fit into the opening 60 as shown in the dotted lines in FIG. 14, whereupon the dogs 104 of the release mechanism 92 shift into the slots 106 to hold the filler section 20D in place. When the handle 102 of the release mechanism is actuated, the dogs release and the filler section 20D may drop and slide back beneath the spine 52.

Figure 16:
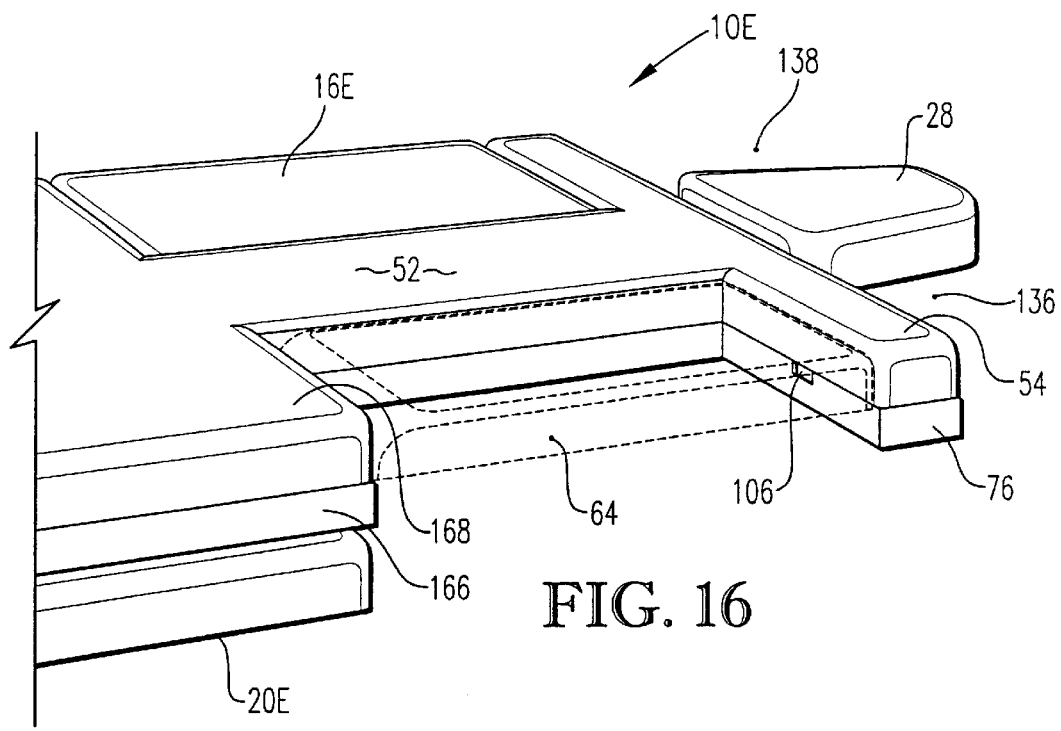
FIG. 16 is a fragmentary upper side perspective view of the embodiment of FIG. 15, showing the filler section in a stowed position in solid lines and in an opening occupying position in phantom lines.

FIGS. 15 and 16 show a sixth embodiment of the apparatus 10E which includes mount 154 and is similar to the apparatus 10D shown in FIGS. 12, 13 and 14, except that one or more of the filler sections, e.g. filler section 20E, has mount 154 coupled to a widened center cross channel 166, and the filler section 20E drops and translates in a longitudinal direction for stowage beneath the central support arm 168 as shown in FIG. 16. The release mechanism 170 thus includes only a single latch 172 whose dogs enter into the opposite end cross channel 76.

Figure 17:
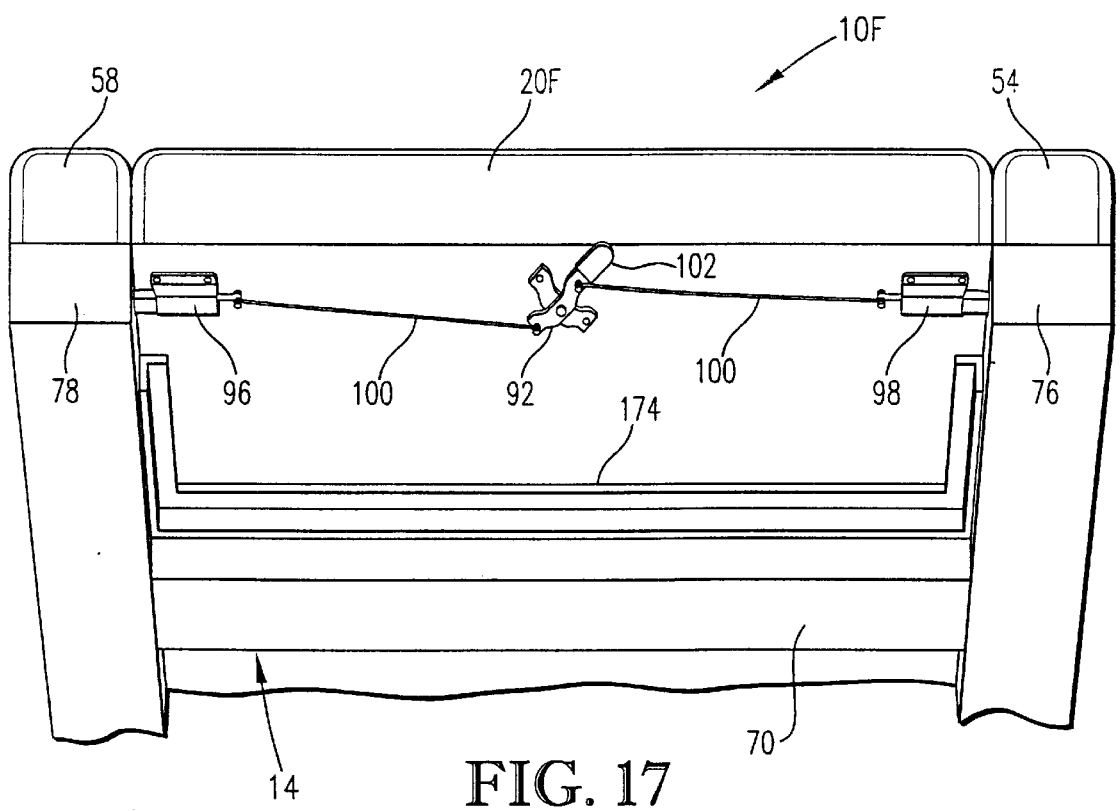
FIG. 17 is a fragmentary bottom side perspective view of a seventh embodiment of the apparatus hereof, wherein the filler section is supported by a release mechanism and support ledge to enable removal from the frame when the opening is to be cleared.

FIG. 17 illustrates a seventh embodiment of the apparatus 10F, with one or more of the filler sections, e.g. filler section 20F, being removably mounted to the frame 14. A U-shaped ledge 174 is welded or fastened to the rail 68, center cross channel 78 and end cross channel 76, whereby actuating the release mechanism 92 enables the filler section 20F to be lifted or slide outwardly and removed from the apparatus 10F to clear the opening 60. In additional embodiments, the apparatus 10F might have no locking release mechanism and be held in place simply by resting on a U-shaped ledge 174. Further, the sides of the filler section might be provided with a normally medial to lateral extending slot to allow the filler section to slide into and out of sliding engagement with the deck on U-shaped ledge 174. Finally, in the simplest variation on this embodiment, the deck 12 might have no filler sections and merely utilize unfilled openings to accommodate and receive therein the patient, portions of the mammography device 36, or medical personnel such as a technician.

Figure 18:
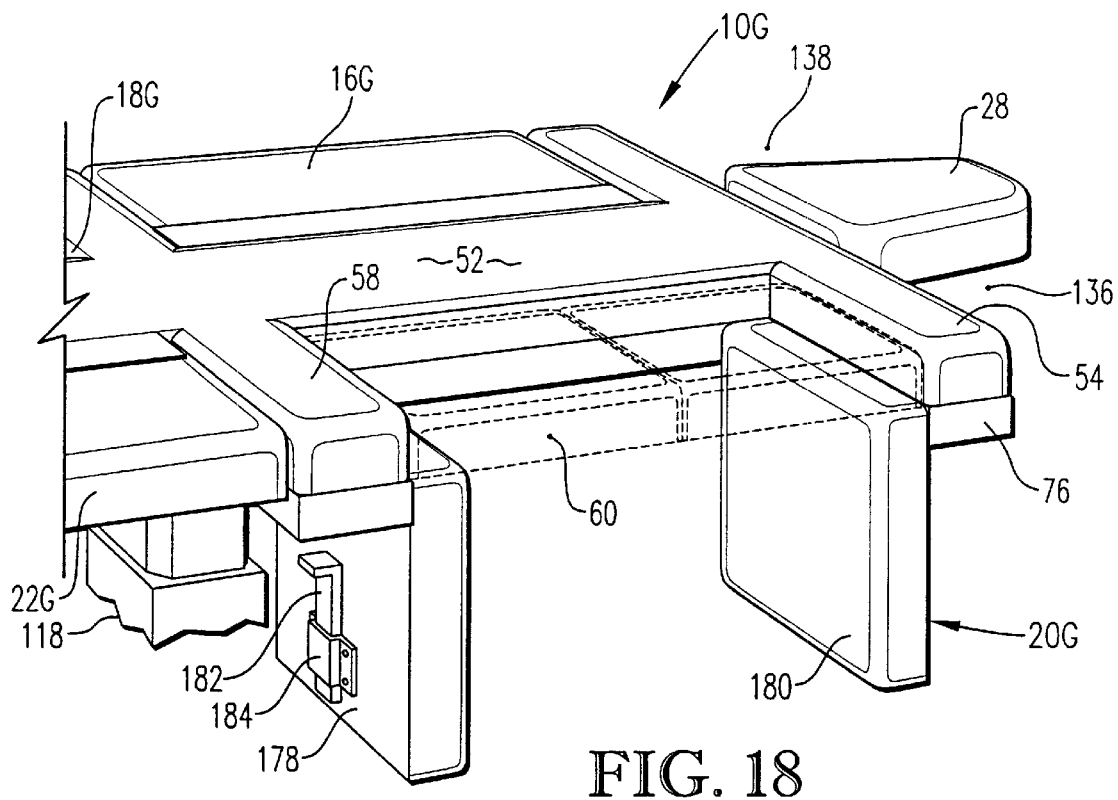
FIG. 18 is a fragmentary top side perspective view of an eighth embodiment of the apparatus hereof, wherein the apparatus is provided with two opposed filler section halves each pivoting on parallel axes and shown in position to provide access to the opening, and provided with a coupling bar for securing the filler section halves when pivoted upwardly to a horizontal orientation.
Figure 19:
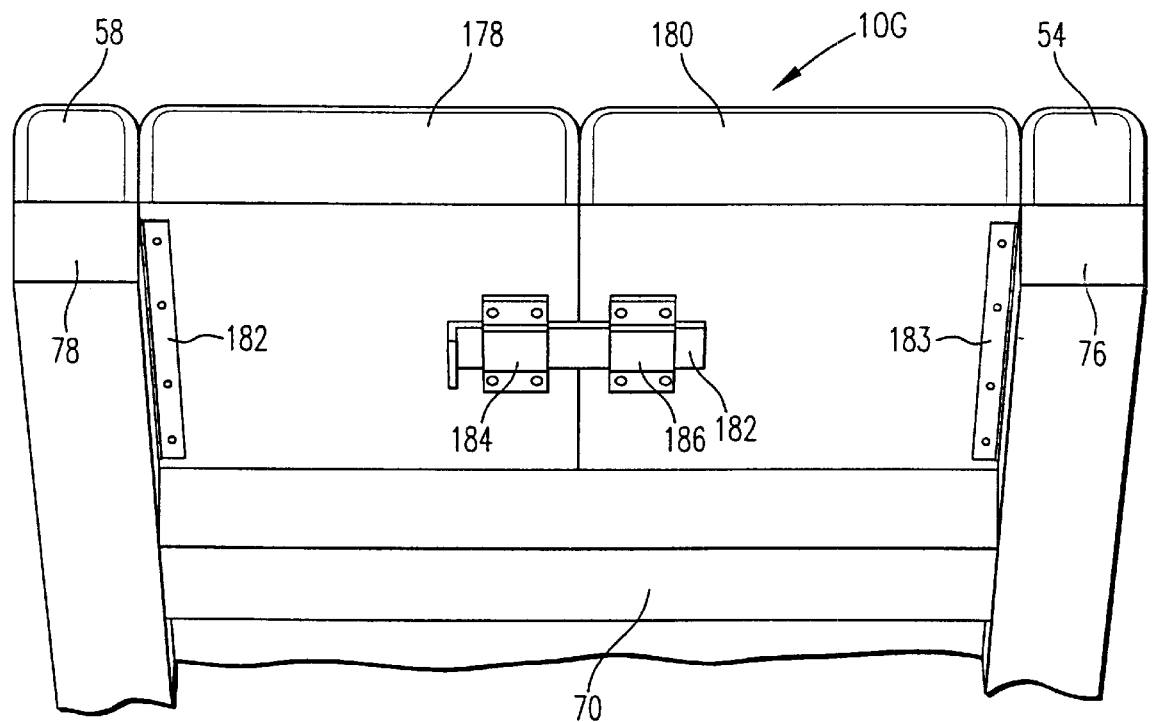
FIG. 19 is a fragmentary bottom side perspective view of the embodiment of FIG. 18, wherein the filler section halves are pivoted into a closed position and secured by the coupling bar.

FIGS. 18 and 19 illustrate an eighth embodiment of the apparatus 10G, with one or more of the filler sections bifurcated and separately hinged. Filler section 20G has filler section halves 178 and 180 each have a respective hinge 182 and 184 secured by welding or fasteners to the center cross channel 78 and end cross channel 76 respectively. The filler section halves 178 and 180 together occupy opening 60 when raised into a horizontal orientation as shown in FIG. 19, and may be held in place by latching bar 182 shiftably received in brackets 184 and 186 and upon which a part of the load applied to the filler section halves is borne.

Figure 20:
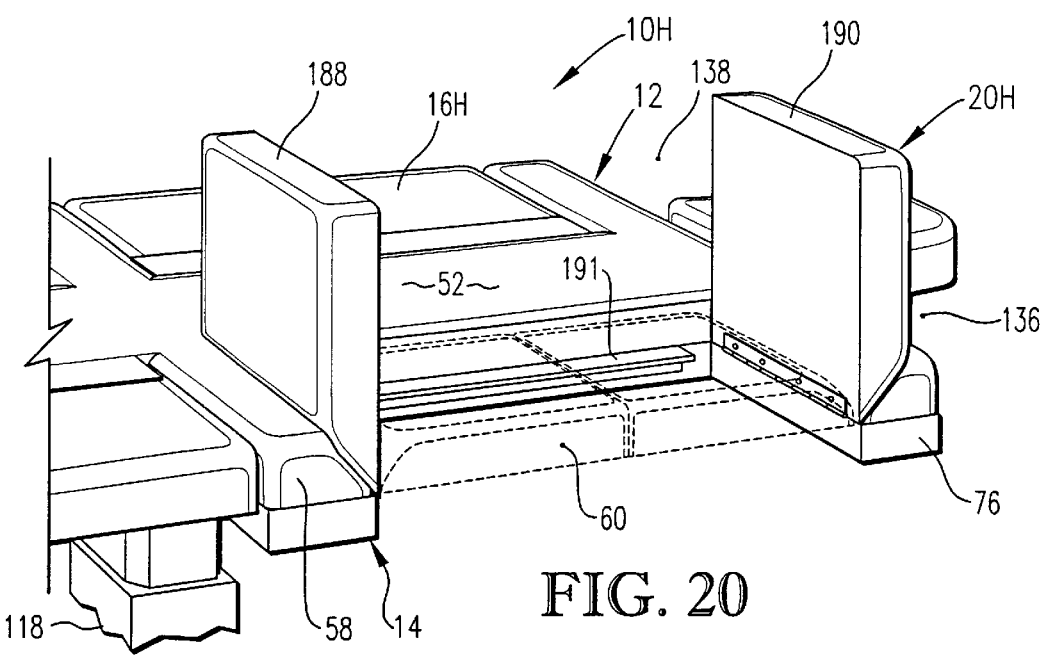
FIG. 20 is a fragmentary top side perspective view of a ninth embodiment of the apparatus hereof, wherein the apparatus is provided with two filler section halves for pivoting upwardly along opposed parallel axes.
Figure 21:
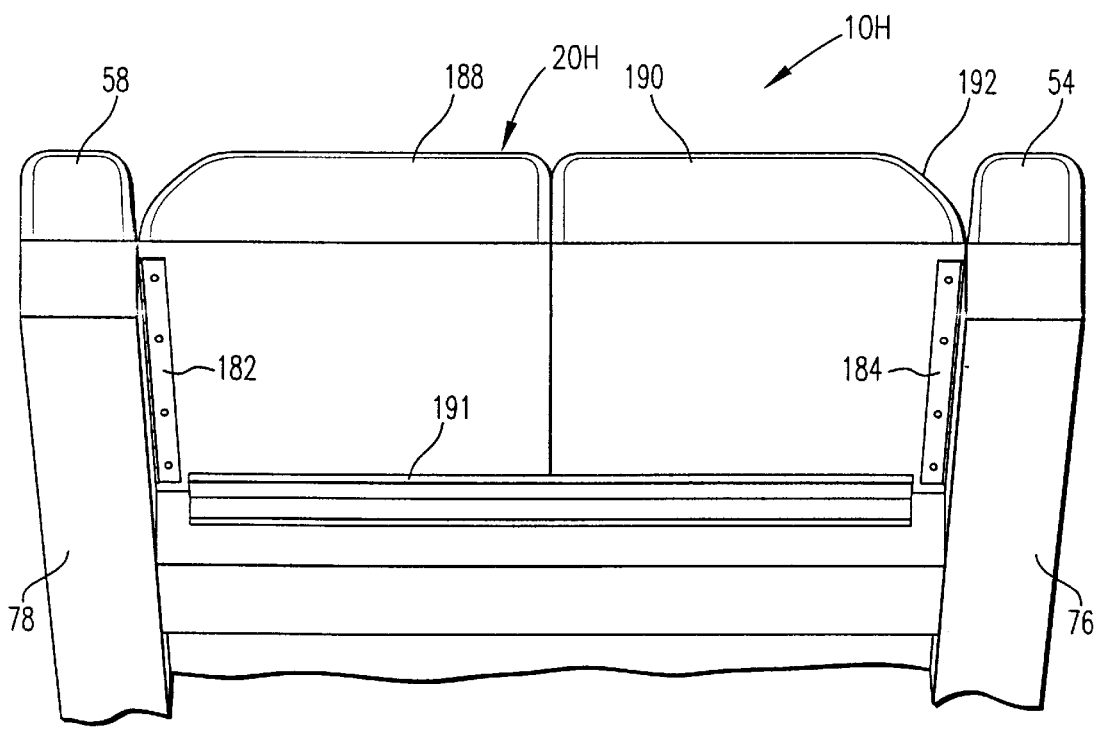
FIG. 21 is a fragmentary bottom side perspective view of the embodiment of FIG. 20, showing the filler section halves in a closed position and supported on a ledge coupled to the frame.

FIGS. 20 and 21 illustrate an ninth embodiment of the apparatus 10H, wherein one or more of filler sections, e.g. the filler section 20H, again has filler section halves 188 and 190 which are similar to filler section halves 178 and 180 but have a tapered upper surface 192 adjacent the central support arm 58 and first outer support arm 54, respectively. The hinges 182 and 184 thus permit the filler section halves 188 and 190 to swing upwardly to clear the opening 60 as shown in FIG. 20, and a ledge 191 is secured by welding or fasteners to rail 68 to support the filler section halves 188 and 190 when in a horizontal position as shown in FIG. 21.

Figure 22:
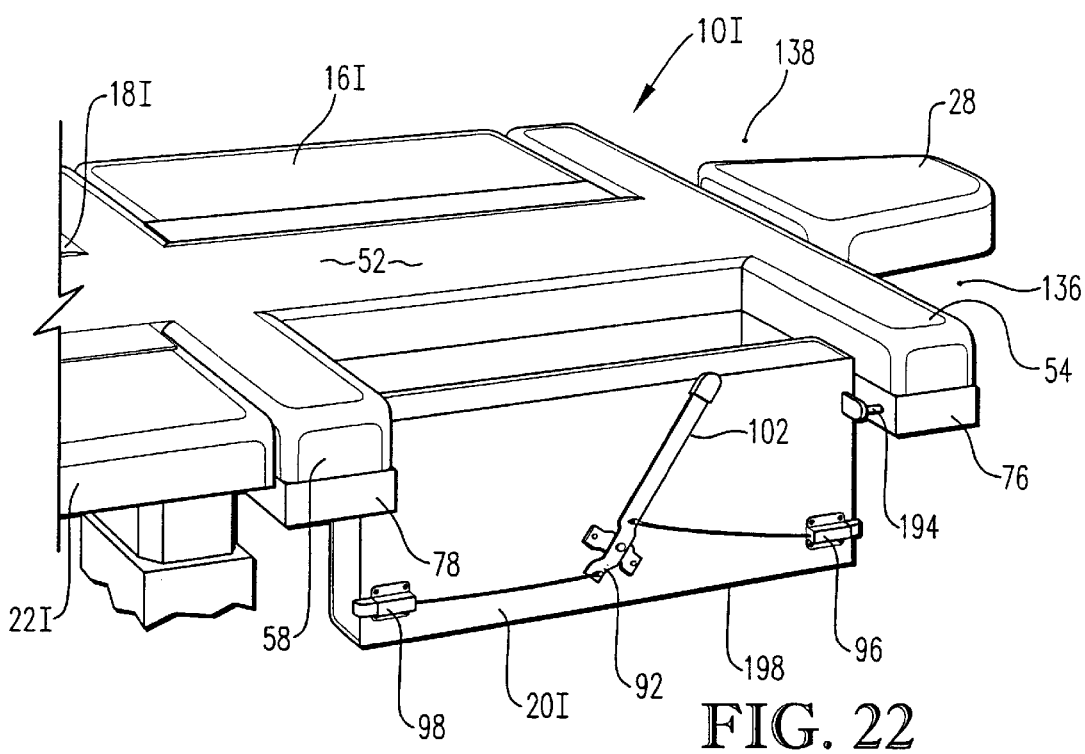
FIG. 22 is a fragmentary top side perspective view of a tenth embodiment of the apparatus hereof, wherein the apparatus has a filler section which pivots about an outboard axis proximate the ends of the crossbars.
Figure 23:
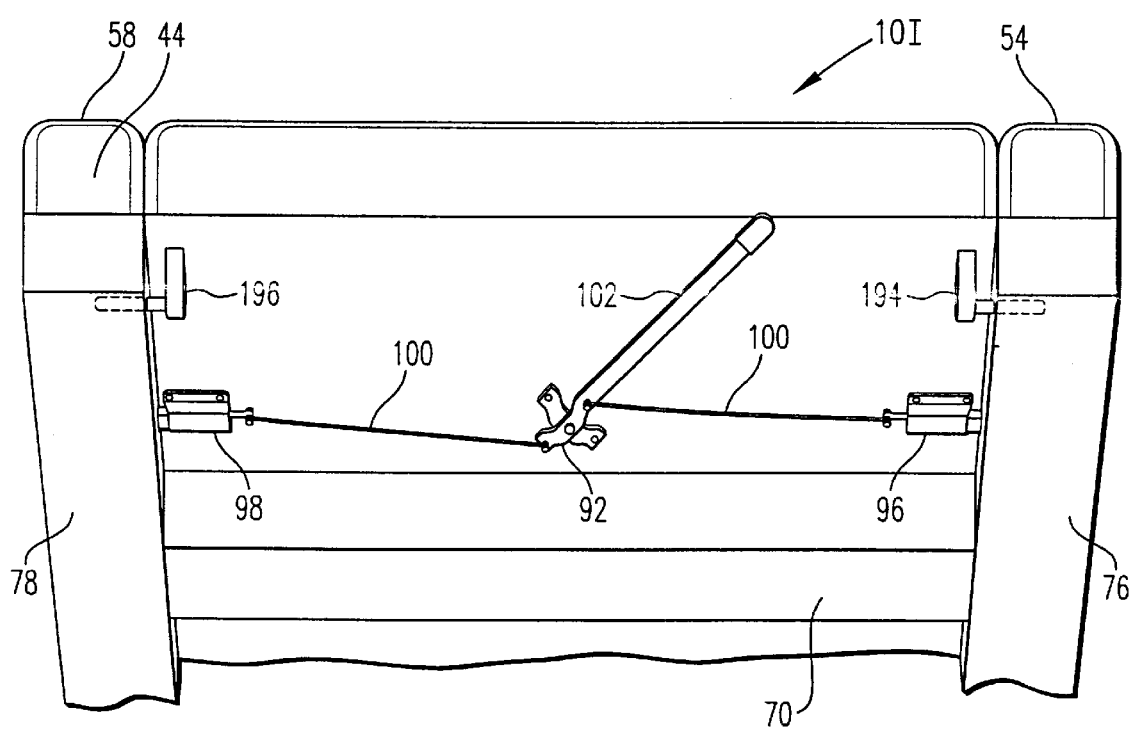
FIG. 23 is a fragmentary bottom side perspective view of the embodiment of FIG. 22, showing the pivotal mount and release mechanism for supporting the filler section when in a horizontal orientation.

FIGS. 22 and 23 illustrate a tenth embodiment of the apparatus 10I, wherein pivot mounts 194 and 196 pivotally connect the filler section 20I adjacent the first side 44 of each the end cross channel 76 and the center cross channel 78. The release mechanism 92 is thus modified with a longer handle 102, with the latches 96 and 98 located inboard of the pivot mounts 194 and 196 to permit the filler section 20I to pivot and drop at its inboard edge 198.

Figure 24:
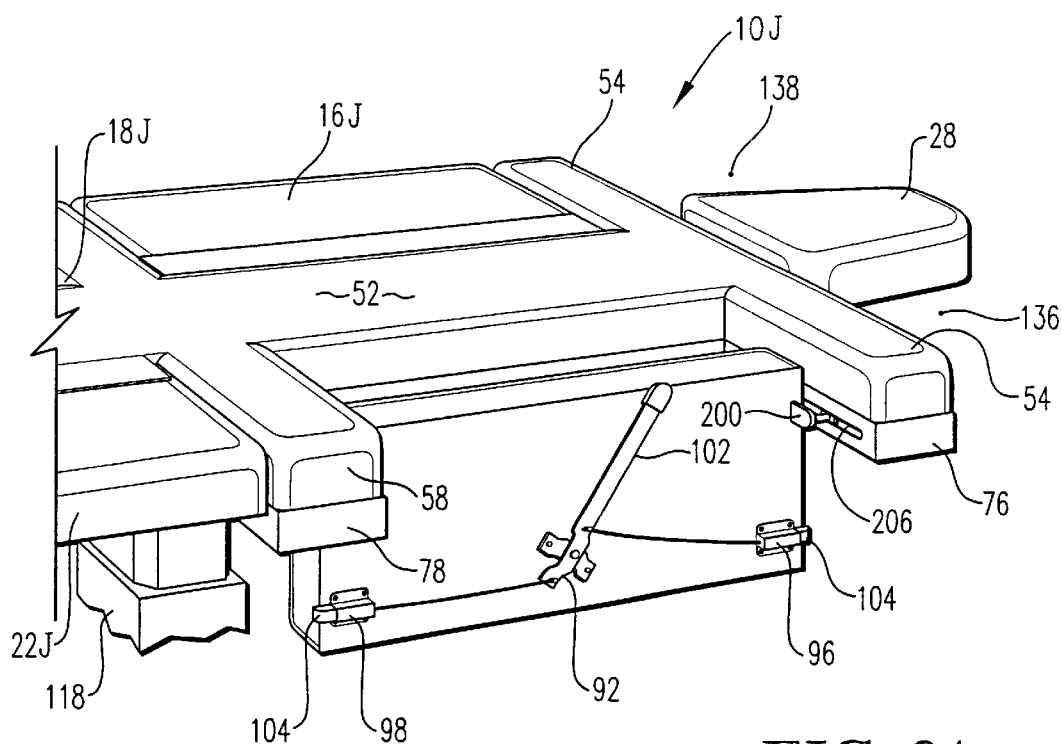
FIG. 24 is a fragmentary top side perspective view of an eleventh embodiment of the apparatus hereof, wherein the apparatus mounts a filler section to pivot and translate toward the central spine to clear the opening.
Figure 25:
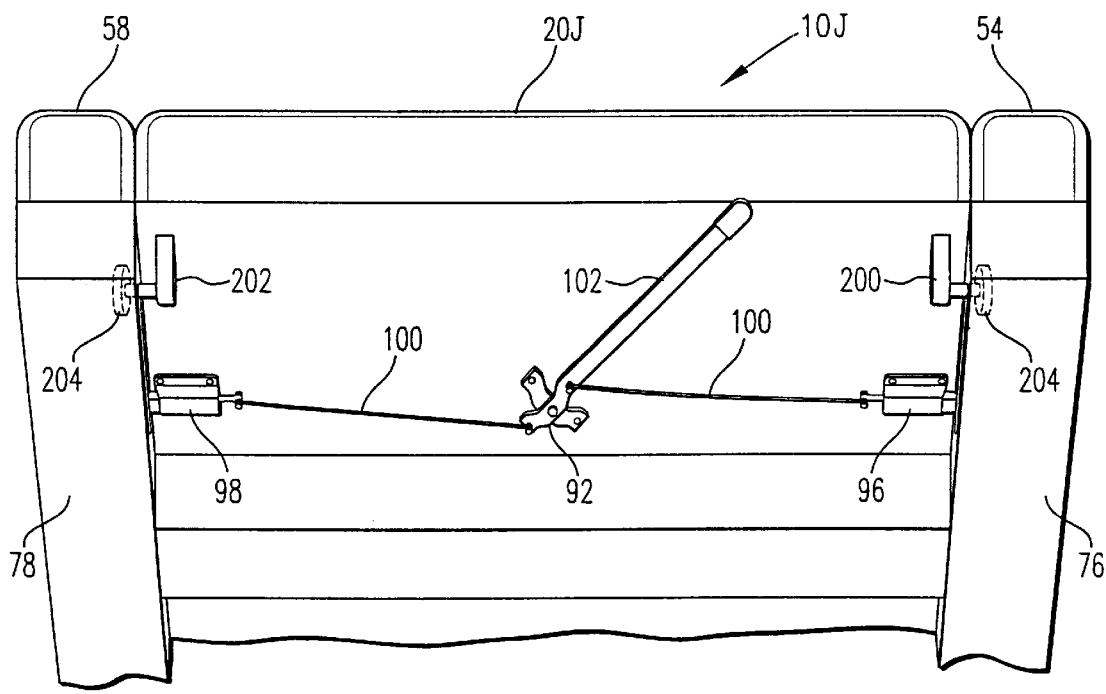
FIG. 25 is a fragmentary bottom side perspective view of the embodiment of FIG. 24, showing roller mountings for enabling the filler section to slide inwardly after pivoting downwardly to clear its corresponding opening

FIGS. 24 and 25 illustrate an eleventh embodiment of the apparatus 10J, similar to apparatus 10I, but wherein one or more of the filler sections, e.g. filler section 20J, has pivot mounts 200 and 202 each provided with rollers 204. The rollers 204 are received within the tubular end cross channel 76 and center cross channel 78 and free to roll in a lateral direction transverse to the longitudinal axis of the apparatus 20J therewithin. The end cross channel 76 and center cross channel 78 are provided with laterally extending slots 206 whereby the pivot pins 208 of the pivot mounts 200 and 202 may traverse along the slots. Upon actuation of the release mechanism 92, the filler section 20J is free to pivot and drop along its inboard edge 198, and then translate along the slots 206 to clear the opening 60.

As a result of the configuration and operation of the apparatus 10 hereof, mammography and breast biopsy may be performed with patients in the decubitus position even in relatively small rooms. By permitting ingress of the mammography device into one of the openings of the apparatus 10, and by providing multiple openings, the apparatus facilitates its positioning in a variety of orientations according to the size of the equipment and comfort to the patient. Because the head and foot supports are interchangeable, the patient may remain comfortable in either the left decubitus or right decubitus position when the apparatus 10 and the mammography device 36 are restricted in their ability to be repositioned because of the tight space. The spine and cross-members of the frame still provide firm and stable support so that the patient does not become anxious when a filler section is dropped to clear an opening. The openings and the ability of the pedestal 118 to move the frame and the filler sections up and down enables the technician to have the most favorable access and positioning relative to the patient. Moreover, by providing openings complementally sized to receive either the camera portion or film cassette portion of the mammography device 36, the mammography device 36 may be tilted in a direction 180° from that shown in FIG. 2 with the camera portion 132 located in opening 62 and the cassette portion 134 located in opening 60 whereby caudal-cranial imaging of a patient in a right lateral decubitus position may be performed.

Although preferred forms of the invention have been described above, it is to be recognized that such disclosure is by way of illustration only, and should not be utilized in a limiting sense in interpreting the scope of the present invention. Obvious modifications to the exemplary embodiments, as hereinabove set forth, could be readily made by those skilled in the art without departing from the spirit of the present invention.

The inventors hereby state their intent to rely on the Doctrine of Equivalents to determine and assess the reasonably fair scope of their invention as pertains to any apparatus not materially departing from but outside the literal scope of the invention as set out in the following claims.

What is claimed is:

1. In combination:
    a mammography device including a first image receptor portion and a second camera portion; and
    a patient support apparatus comprising:
        a deck sized to support an adult human in a lateral decubitus position thereon, said deck including longitudinally spaced first and second ends and laterally spaced first and second sides, said first side including at least one recess therein defining a first opening complementally sized to receive said first portion of said mammography device medial to said first side, wherein a breast of the human may be positioned adjacent said opening on said first portion of said mammography device while the human is in a lateral decubitus position supported by the deck.

2. The combination of claim 1, wherein the opening is sized to permit positioning of the first portion of the mammography device in the opening in an orientation for lateral-medial imaging of a uppermost breast of a human supported on the apparatus in a decubitus position.

3. The combination of claim 2, wherein the opening is sized to permit positioning of the first portion of the mammography device in the opening in an orientation for medial-lateral imaging of the lowermost breast of a human supported on the apparatus in a decubitus position.

4. The combination of claim 3, wherein the opening is sized to permit positioning of the first portion of the mammography device in the opening in an orientation for oblique angle imaging of one of the uppermost and lowermost breast of a human supported on the apparatus in a decubitus position.

5. The combination of claim 4, wherein the opening is sized to permit positioning of the first portion of the mammography device in the opening with said second portion positioned to permit stereo imaging of one of the uppermost and lowermost breast of a human supported on the apparatus in a decubitus position.

6. The combination of claim 1, wherein the apparatus includes a head support coupled to one end of the deck, the head support having a transverse dimension substantially less than the transverse dimension between said first and second sides to permit positioning of the second portion of said mammography device adjacent said head support during cranial-caudal imaging of a breast of a human supported on the apparatus in a decubitus position and the breast positioned adjacent said opening on said first portion.

7. The combination of claim 6, wherein the head support is sized to permit positioning of the second portion of said mammography device adjacent the head support and below the deck during stereo imaging of the breast positioned adjacent said opening on said first portion.

8. The combination of claim 6, wherein the head support includes a coupler for permitting the head support to be vertically adjustable relative to said deck.

9. The combination of claim 1, wherein the first side including a second recess therein defining a second opening complementally sized to receive the second portion of the mammography device therein to permit caudal-cranial imaging of one of the uppermost and lowermost breast of a human supported on the apparatus in a decubitus position.

10. The combination of claim 1, wherein the apparatus includes a second recess in said first side defining a second opening complementally sized to receive said first portion of said mammography device medial to said first side, wherein a breast of the human may be positioned adjacent said second opening on said first portion of said mammography device while the human is in a lateral decubitus position supported by the deck.

11. The combination of claim 10, wherein the apparatus includes a head support and first and second mounts respectively positioned at said first and second ends adapted for removably coupling said head support to the deck alternately at either said first or second end, whereby the human may be supported by the apparatus in a decubitus position with said human's head at either said first end or said second end.

12. The combination of claim 1, wherein the apparatus includes a second recess in said first side defining a second opening sized to receive a portion of an examiner therein for positioning the examiner medial to said first side and enabling the examiner to be located proximate the first portion of the mammography device.

13. The combination of claim 1, wherein the apparatus includes a recess in said second side defining a second opening sized to receive a portion of an examiner therein for positioning the examiner medial to said second side and enabling the examiner to be located proximate the first portion of the mammography device.

14. The combination of claim 1, wherein the apparatus includes a second recess in said second side defining a second opening complementally sized to receive said first portion of said mammography device medial to said second side, said second opening being substantially opposite to said first opening, whereby a human supported on said deck in a left or right lateral decubitus position with a first breast in an upper position in the first opening may roll about the longitudinal axis and position a second breast in an upper position in the second opening in an alternate lateral decubitus position.

15. The combination of claim 14, wherein the apparatus includes a third recess, said third recess being positioned in said first side defining a third opening longitudinally spaced from said first opening and complementally sized to receive said first portion of said mammography device medial to said first side.

16. The combination of claim 14, wherein the apparatus includes a third recess, said third recess being positioned in said first side defining a third opening longitudinally spaced from said first opening and sized to receive an examiner medial to said first side and enabling the examiner to be located proximate the first portion of the mammography device.

17. The combination of claim 15, wherein the apparatus includes a fourth recess, said fourth recess being positioned in said second side defining a fourth opening longitudinally spaced from said second opening and across from said third opening and complementally sized to receive said first portion of said mammography device medial to said second side.

18. The combination of claim 15, wherein the apparatus includes a fourth recess, said fourth recess being positioned in said second side defining a fourth opening longitudinally spaced from said second opening and across from said third opening and sized to receive an examiner medial to said second side.

19. The combination of claim 17, wherein the apparatus includes first, second, third and fourth filler sections complementally configured for receipt in said openings, each said filler sections being coupled to said deck when received in said openings.

20. The combination of claim 19, wherein at least one of said filler sections is removably coupled to said deck.

21. The combination of claim 19, wherein at least one of said filler sections is pivotally mounted to said deck.

22. The combination of claim 21, wherein at least one of said filler sections pivots downwardly to clear said opening.

23. The combination of claim 21, wherein at least one of said filler sections pivots upwardly to clear said opening.

24. The combination of claim 19, wherein at least one of said filler sections is coupled for translation relative to said deck.

25. The combination of claim 1, wherein said deck includes a mount located at each said first end and said second end, and including a foot support removably coupled to one of said mounts and a head support removably coupled to the other of said mounts, wherein said foot support and said head support are adapted for coupling to mounts at either said first end or said second end.

26. The combination of claim 25, wherein said foot support and head support each have transverse dimensions, the transverse dimension of the head support being substantially less than the transverse dimension between said first and second sides, the transverse dimension of the foot support being greater than the transverse dimension of the head support.

* * * * *

UNITED STATES PATENT AND TRADEMARK OFFICE
CERTIFICATE OF CORRECTION

PATENT NO. : 6,557,196 B2 Page 1 of 1
APPLICATION NO. : 10/038481
DATED : May 6, 2003
INVENTOR(S) : Michael G. Falbo, Sr.

It is certified that error appears in the above-identified patent and that said Letters Patent is hereby corrected as shown below:

On Title Page Item [63]

Please correct Continuation Data from: "Continuation of Application No. 09/712,475 filed on November 14, 2000 now Patent No. 6,367,104 which is a continuation of Application No. 09/611,983 filed on July 7, 2000 now Pat. No. 6,317,266" to --Continuation of application No. 09/712,475 filed on November 14, 2000, now Patent No. 6,367,104, which is a continuation of application No. 09/611,983, filed on July 7, 2000 now abandoned.--

Signed and Sealed this

Fifteenth Day of April, 2008

JON W. DUDAS
*Director of the United States Patent and Trademark Office*